United States Patent
Kemp et al.

(10) Patent No.: US 6,886,208 B2
(45) Date of Patent: May 3, 2005

(54) TOOTHBRUSH ASSEMBLY HAVING AN ENVIRONMENTALLY SAFE POLYMER BATTERY

(75) Inventors: James Kemp, Somerset, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/506,057

(22) PCT Filed: Nov. 7, 2003

(86) PCT No.: PCT/US03/35521
§ 371 (c)(1), (2), (4) Date: Aug. 27, 2004

(87) PCT Pub. No.: WO2004/043204
PCT Pub. Date: May 27, 2004

(65) Prior Publication Data
US 2005/0034256 A1 Feb. 17, 2005

Related U.S. Application Data
(60) Provisional application No. 60/424,924, filed on Nov. 8, 2002.

(51) Int. Cl.[7] .......................... A46B 9/04; A46B 15/00
(52) U.S. Cl. ...................................... 15/167.1; 15/105
(58) Field of Search ............................. 15/105, 167.1

(56) References Cited

U.S. PATENT DOCUMENTS

| | | |
|---|---|---|
| 4,485,796 A | 12/1984 | Boyer |
| 4,801,512 A | 1/1989 | MacDiarmid et al. |
| 4,804,594 A | 2/1989 | Taiguang et al. |
| 5,070,567 A | 12/1991 | Holland |
| 5,339,479 A | 8/1994 | Lyman |
| 5,390,984 A | 2/1995 | Boucherie et al. |
| 5,416,942 A | 5/1995 | Baldacci et al. |
| 5,527,640 A | 6/1996 | Rudge et al. |
| 5,533,791 A | 7/1996 | Boucherie |
| 5,609,890 A | 3/1997 | Boucherie |
| 5,625,916 A | 5/1997 | McDougall |
| 5,665,490 A | 9/1997 | Takeuchi et al. |
| 5,733,683 A | 3/1998 | Searson et al. |
| RE35,941 E | 11/1998 | Stansbury, Jr. |
| 5,888,672 A | 3/1999 | Gustafson et al. |
| 6,032,213 A | 2/2000 | Gulick |
| 6,106,294 A | 8/2000 | Daniel |

FOREIGN PATENT DOCUMENTS

JP  1-129803  5/1989

*Primary Examiner*—Randall Chin
(74) *Attorney, Agent, or Firm*—Harris A. Wolin; Clifford E. Wilkins

(57) ABSTRACT

The present invention discloses a powered or manual toothbrush having a polymer battery as a power source. The polymer battery contains no heavy metals, making it environmentally safe, and contains no alkaline, making it physically safe. The polymer battery is inexpensive and rechargeable, making it an economical power source for the toothbrush. The small size of the polymer battery saves space in the toothbrush housing, enabling the housing to be smaller and saving on materials of construction. The flexible nature of the polymer battery enables it to be shaped to fit into or around the periphery of the toothbrush housing design.

20 Claims, 1 Drawing Sheet

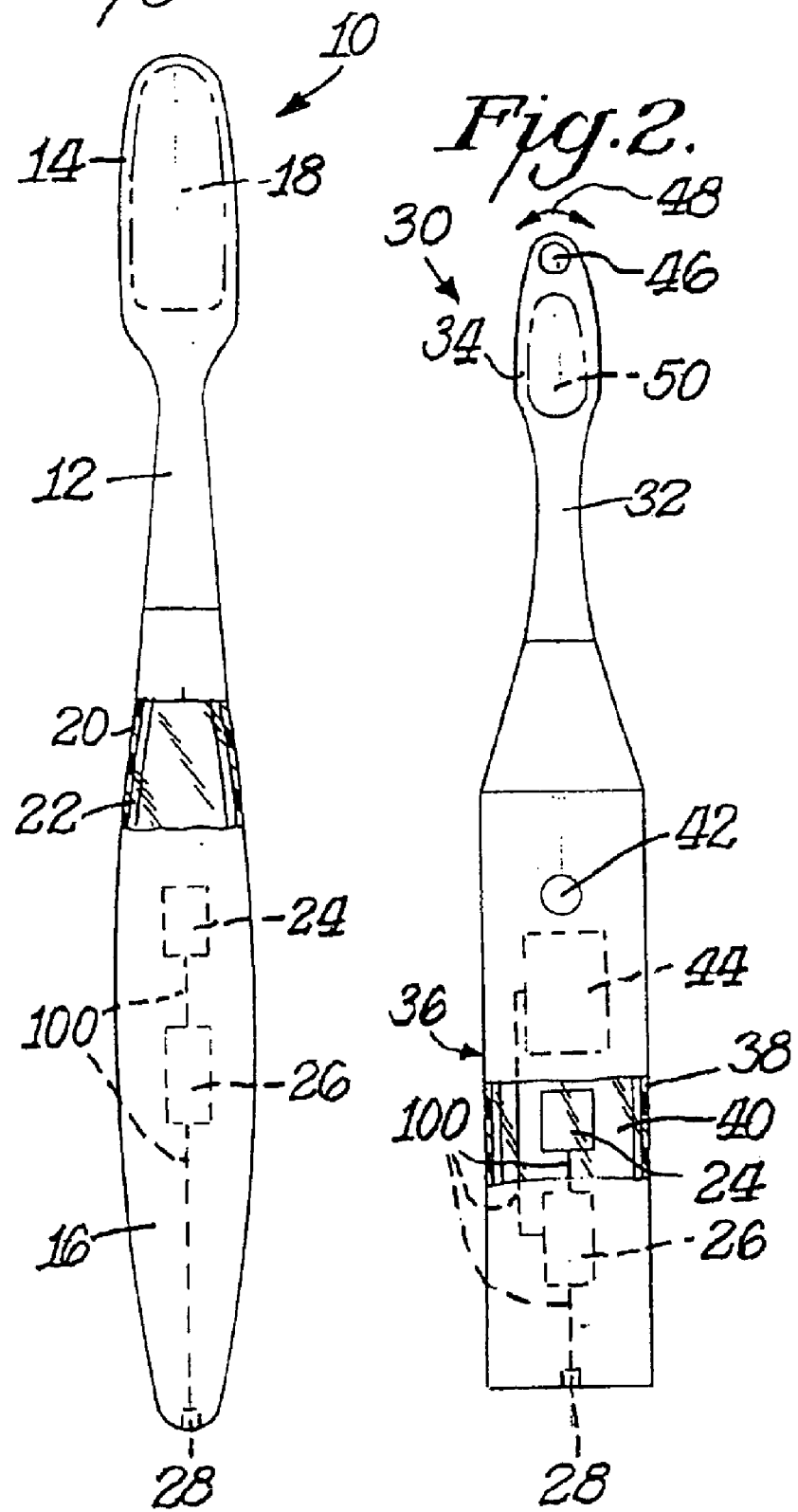

TOOTHBRUSH ASSEMBLY HAVING AN ENVIRONMENTALLY SAFE POLYMER BATTERY

This application is a 371 of PCT/US05/35521 filed Nov. 7, 2003, which claims the benefit of U.S. Provisional Application No. 60/424,924 filed Nov. 8, 2002.

BACKGROUND OF THE INVENTION

A. Field of the Invention

The present invention relates generally to toothbrushes, and, more particularly, to a toothbrush assembly having an environmentally safe polymer battery.

B. Description of the Related Art

Many conventional toothbrushes use batteries to power movable bristles and/or to illuminate light sources provided in the toothbrush handle. For example, various types of powered toothbrushes are generally known in the art. U.S. Pat. No. 5,625,916 discloses an electrically driven toothbrush having a motor drive for rotating a drive shaft. The drive shaft connects to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

U.S. Pat. No. 5,416,942 shows a further type of powered toothbrush wherein the head includes a pair of concentrically arranged sections, each of which is driven in a rotationally oscillating manner in opposite directions.

U.S. Pat. No. 6,032,313 discloses a household appliance such as a toothbrush that may be used for cleaning, polishing, or massaging. The head of the appliance includes a plurality of co-axially rotatable or parallel linearly-movable sections, but fails to provide other bristle-containing sections.

U.S. Pat. No. 5,070,567 discloses an electrically-driven toothbrush that includes a rotatable brush head having bristles thereon. A further group of bristles, each of which rotates around its own axis, reside adjacent to the brush head.

Known illuminated toothbrush constructions include an enlarged handle housing circuitry connected to a battery for powering small light bulbs mounted in the handle wall to form a plurality of light points on the surface of the toothbrush. This is seen in U.S. Pat. Nos. 4,845,796 and 5,339,479. The purpose of such a construction is, at least partially, to motivate children to brush their teeth, as the pinpoints or discrete areas of light are deemed to add an element of interest and novelty to the brushing process, offering a fun and exciting way for children to brush their teeth. Such excitement motivates children to brush their teeth often, to set in place lifelong habits of good oral hygiene. Standard micro batteries may be used to provide sufficient power to illuminate the toothbrush during brushings for six to twelve months, which is about the normal useful life of a toothbrush. However, replacement batteries may also be used.

All of these toothbrush patents disclose use of conventional batteries. Unfortunately, conventional batteries (e.g., alkaline batteries) have their shortcomings. First, they are not physically or environmentally safe. Potassium hydroxide electrolyte, a strong alkali, is contained within the cells of the batteries. If alkaline batteries are damaged or mishandled, the potassium hydroxide may leak out of the battery cell. Severe chemical burns can result if potassium hydroxide comes into contact either skin or eyes. Conventional batteries account for a significant percentage of heavy metal contaminants in landfills and incinerators. The major concern with consumer batteries in landfills is their corrosiveness and toxic heavy metal content. As the batteries are damaged or corroded, the contents spill into the environment. Second, conventional batteries used for toothbrushes (e.g., AA batteries) are typically not small in size. Finally, conventional toothbrush batteries are not flexible, but rather contain rigid housings (e.g., housings of nine-volt batteries).

A promising application of conducting polymers is in energy storage devices. Battery systems have been extensively studied where a p-dopable conducting polymer is uses as the cathode active material and a metal, often lithium, is used as the anode active material. Various p-dopable materials have been studied: polyacetylene, poly-(p-phenylene), polypyrrole, polyaniline, etc. A battery with n-dopable conducting polymer, polyacetylene, as the anode material and a metal oxide as cathode active material has also been described. Such batteries may be constructed from multiple polymer films, making them lightweight and flexible. Since polymer batteries are moldable into various shapes and flexible, they may be incorporated into compact devices and take up much less space. These polymeric batteries have remarkably high charge capacities, and excellent cycling efficiency. The provision of polymeric materials further permits the polymeric battery to be substantially free of metal components, thereby improving handling of the battery and obviating the safety and environmental concerns associated with conventional batteries. Various types of polymer-based batteries are known in the art, as shown in U.S. Pat. Nos. 4,801,512, 4,804,594, 5,527,640, 5,665,490, 5,733,683, and 5,888,672.

Despite the desirable features of polymer batteries, none of toothbrush art discloses a toothbrush (manual or powered) that uses an environmentally safe polymer battery. Thus, there is a need in the art for a toothbrush that uses such a battery. Such polymer batteries contain no heavy metals making them environmentally safe; are low in cost; are small in size, saving space in the toothbrush housing and enabling the housing to be smaller (saving on materials of construction); can be shaped to fit into the housing design; and exhibit high charging capacities with excellent cycling efficiencies.

SUMMARY OF THE INVENTION

The present invention solves the problems of the related art by providing a toothbrush having a polymer battery as a power source. The polymer battery contains no heavy metals, making it environmentally safe, and contains no alkaline, making it physically safe. The polymer battery is inexpensive and, preferably, rechargeable, making it an economical power source for the toothbrush. The small size of the polymer battery saves space in the toothbrush housing, enabling the housing to be smaller and saving on materials of construction. The flexible nature of the polymer battery enables it to be shaped to fit into or around the periphery of the toothbrush housing design.

In a first embodiment of the invention, a manual, light interactive toothbrush is formed of generally conventional form and shape. The toothbrush handle may be provided internally with a small light source, such as a light emitting diode (LED), electrically coupled to a polymer battery. The manual toothbrush handle may be molded with an inner body of transparent or translucent plastic material and an opaque outer layer formed with discrete, spaced-apart openings or windows on its surface. The openings expose the surfaces of the plastic inner body beneath, which may be roughened to emit a softened, diffused light through the windows. Light from the LED travels along the length of the handle and is internally reflected such that reflected light rays striking the roughened windows exposed through the opaque outer layer can emit light at discrete points on the handle and, if desired, also at the head. A highly reflective coating may be applied over the plastic inner body and under the opaque outer coating, except at those areas used for the light points or windows, to ensure that most of the light is reflected down the length of the handle and not substantially absorbed by the opaque outer coating. Reflective patches may be applied over areas of the handle which are positioned to gather and direct light toward the windows in the handle surface.

In a second embodiment of the present invention, a powered toothbrush may be formed of generally conventional form and shape. The powered toothbrush handle may be provided internally with a small light source, such as an LED, electrically coupled to a polymer battery, as well as a drive mechanism, such as a drive shaft rotated by a driving motor, also electrically coupled to the polymer battery. If the powered toothbrush is provided with a light source, then preferably the powered toothbrush handle will have the same configuration as the manual toothbrush handle, as described in the first embodiment of the invention. If the powered toothbrush is not provided with a light source, then the powered toothbrush handle will take on a conventional powered toothbrush configuration, and the polymer battery will be used solely to provide power to the drive mechanism.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a top plan view of a manual lighted toothbrush using a light source and a polymer battery in accordance with an embodiment of the present invention; and FIG. 2 is a top plan view of a powered lighted toothbrush using a light source and a polymer battery in accordance with another embodiment of the present invention.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

FIG. 1 illustrates one practice of the present invention wherein a manual toothbrush 10 includes a neck section 12 interposed between a head 14 and a handheld handle 16. Preferably, neck 12 and head 14 are integrally connected, and together are detachably connected to handle 16 so that head 14 may be replaced as the bristles become worn. In an alternate, less costly embodiment of the present invention, the head 14 and neck 12 are integrally and permanently connected to the handle 16.

As further shown in FIG. 1, handle 16 is provided with an outer covering of an opaque material, such as a hard rubber or rubberized plastic coating, denoted as 20, with an inner body 22 of handle 16 being formed of a transparent or translucent plastic material. A light source 24, such as an LED, may be provided, and preferably molded into handle 16 with a polymer battery 26, and a switch for turning light source 24 on and off. Polymer battery 26 electrically couples to light source 24, via electrical connection 100, to provide power thereto, and electrically couples to a recharge plug in 28, via electrical connection 100, for recharging polymer battery 26.

Light from light source 24 is reflected along the length of the inner body 22 by internal reflection. Covering 20 may be provided with a plurality of openings or windows, each of which exposes the surface of the light-transmissive inner body 22 through the covering 20. The exposed surfaces of the plastic inner body 22 may be roughened so that a softened diffused glow is emitted through the surface of handle 16 at the desired points of light.

A highly reflective layer, such as aluminum foil or metalized coating, may be applied over the surface of the plastic inner body 22 under the opaque outer covering 20, except at the window areas. The reflective coating serves to reflect substantially all of the light from light source 24 along the length of handle 16, so that a substantial portion is not lost by absorption into opaque outer covering 20. Alternatively, opaque outer covering 20 may be formed with a reflective inner surface such as by having fine reflective particles dispersed therein. The light from light source 24 is transmitted by light-transmissive inner body 22 and reflected by internal reflection from the reflective inner surface. The openings, which are neither coated by reflective layer nor covered by the opaque outer covering 20, as well as the uncovered brush area of head 12 may emit light from the inner body 22.

Head 12 is provided with a tuft or bristle block, denoted generally as 18, that includes a plurality of tufts or bristles. Thus, some of the reflected light from light source 24, reflected along the toothbrush inner body 22, may enter head 12 and exit through the base of translucent or transparent tufts or bristles 18.

Alternatively, instead of relying upon reflected or scattered light within the inner body 22 to pass out through exposed openings in handle 16, a plurality of optical fibers, which may be termed "light pipes," may be molded in place within an opaque plastic material forming handle 16. These optical fibers may be formed of the same transparent or translucent material used to form the light-transmissive inner body 22. The respective input ends of these fibers may be located next to light source 24, and the output ends of the fibers may terminate flush at the chosen areas of the surface of handle 16. The output ends of fibers may be roughened to assist in the diffusion of the exiting light. In this aspect of the invention, handle 16 may be formed of an opaque material such as an elastomer or rubber or an opaque material. This material may be molded around the optical fibers by a known over-molding process.

A second embodiment of the present invention, a powered toothbrush, is shown generally as reference numeral 30 in FIG. 2. Powered toothbrush 30 includes a neck section 32 interposed between a head 34 and a handle 36. Head 34 and neck 32 may be a refill and thus be removably connected to handle 36, or head 34 and neck 32, in an alternative, less costly configuration, may be molded as one unit with and permanently connected to handle 36 within the practice of the present invention.

If powered toothbrush 30 includes a light source, then the configuration and materials making up handle 36 would be identical to those described above for handle 16 of manual toothbrush 10. Thus, handle 36 could include an opaque outer covering 38, and a transparent or translucent inner body 40, as shown in FIG. 2. Handle 36 could also utilize the alternative arrangement with the optical fibers or "light pipes" instead the arrangement shown in FIG. 2. As further shown in FIG. 2, a light source 24, such as an LED, may be provided, and preferably molded into handle 36 with a polymer battery 26 and a drive mechanism 44, and a switch 42 for turning light source 24 and drive mechanism 44 on and off. Polymer battery 26 electrically couples to light source 24, via electrical connection 100, to provide power thereto, and electrically couples to a recharge plug in 28, via electrical connection 100, for recharging polymer battery 26. Polymer battery 26 also electrically couples to drive mechanism 44, via electrical connection 100, to provide power thereto.

If powered toothbrush 30 does not include a light source, then the powered toothbrush handle 36 will take on a conventional powered toothbrush configuration, and polymer battery 26 will be used solely to provide power to drive mechanism 44, the features of which is described more fully below.

As further illustrated in FIG. 2, head 34 includes a first tuft or bristle block 46 which is illustrated as being at the outermost or distal portion of head 34. First tuft block 46 is preferably a disk of circular ring-type shape, and oscillates in a rotational manner as indicated by arrow 48 in FIG. 2. Other shapes may be used for first tuft block 46, such as oval or various regular or irregular shapes. A circular shape for first tuft block 46 is preferred since it requires the least amount of clearance to accommodate the oscillating motion and to potentially accommodate an inner counter-oscillating tuft block.

The outer area of first tuft block 46 may include a multitude of tufts or bristles, arranged in a coarcuate row. Similarly, the inner area of first tuft block 46 may be provided with a plurality of tufts of bristles which are also coarcuate with each other along a circle parallel to the arcuate row of the outer area bristles. The two coarcuate sets of bristles are preferred since such arrangement maximizes use of the surface area of first tuft block 46. In one practice of the present invention, the outer row of bristles extend outwardly from the outer surface of head 34 a greater distance than the inner arcuate row of bristles. As a result, a cup-like structure is formed which facilitates retaining toothpaste on the bristles.

A characteristic of the invention is the provision of a movable second tuft block 50 which is illustrated as being between neck 32 and first tuft block 46. It is to be understood, however, that second tuft block 50 could be located distally from, or laterally side-by-side to first tuft block 46. It is preferred, however, that second tuft block 50 be longitudinally outside of tuft block 46 so as to extend the length of the surface area of head 34 having bristles.

The provision of second tuft block 50 is also advantageous in that powered toothbrush 30 simulates, in appearance of head 34, the structure of a manual toothbrush. This makes powered toothbrush 30 more acceptable to users since the appearance simulates what a user is accustomed to seeing. In addition, the pair of tuft blocks 46, 50 enhances the efficiency of toothbrush 50, both as a result of the movement of tuft blocks 46, 50, and of the ability to readily retain toothpaste.

While conventional fiber form bristles may be used for bristle blocks 18, 46, 50, the term "bristles" as used herein is intended to be used in a generic sense as cleaning elements or massage elements and could include, for example, elastomeric fingers or walls arranged in a circular cross-section shape or any type of desired shape, including straight portions or sinusoidal portions.

The bristles could be mounted to the tuft blocks or sections by extending through suitable openings in the tuft blocks so that the base of the bristles is mounted within or below the tuft blocks. If desired, the bristles could be embedded in an elastomeric material which would permit the bristles to have an independent motion in addition to the motion imparted by the oscillating tuft blocks 46, 50, instead of being fixed bristles. Such various forms of bristles may thus be used for the bristles used in any section of heads 14, 34.

It is to be understood that the specific bristles are merely for exemplary purposes. The invention can, however, be practiced with various combinations of the same or different bristle configurations (such as stapled, in-mold tufting (IMT) technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while the bristles may be generally perpendicular to the outer surface of heads 14, 34, some or all of the bristles may be angled at various angles with respect to the outer surface of the bristle head. It is thereby possible to select the combination of bristle configurations, bristle materials and bristle orientations to achieve specific intended results, such as to create as much movement from the oscillating tuft heads to deliver additional oral health benefits like enhanced cleaning, tooth polishing, tooth whitening and/or massaging of the gums.

It is to be understood that the invention can be practiced by locating tufts of bristles in any otherwise open area of the toothbrush head. Such tufts of bristles could be fixed bristles perpendicularly mounted or mounted at an angle to the exposed outer surface of heads 14, 34, or could be bristles mounted on an elastomeric base so as to be independently movable when pressure is applied. Such bristles in their normal condition could be either perpendicular or at an angle to the exposed outer surface of the toothbrush head.

Tuft blocks 46 and 50 may be oscillated by any suitable drive mechanism 44. For example, the type of drive mechanism described in U.S. Pat. No. 5,625,916, the disclosure of which being incorporated by reference herein in its entirety except where inconsistent with the express teachings of the present invention, may be used for drive mechanism 44. In this arrangement, a drive shaft is rotated by a driving motor provided in handle 36, the driving motor being powered by polymer battery 26. A transmission spindle operatively connects, such as by a permanent or detachable connection, to the drive shaft. The transmission spindle may have two projections oriented eccentrically with respect to the axis of rotation of the drive shaft. A first projection acts as a cam surface and engages an axial slot formed in first tuft block 46. A second projection also acts as a cam surface and engages an axial slot formed in second tuft block 50. Rotation of the drive shaft and transmission spindle results in rotation of the projections. Because the eccentric portions of the projections are mounted in slots of tuft blocks 46, 50, the rotational movement is transmitted to tuft blocks 46, 50 as an oscillating rotational movement to first tuft block 46, as shown by arrow 48 in FIG. 2, and as a side-to-side oscillating movement to second tuft block 50.

Alternatively, tuft blocks 46, 50 could be driven by separate drive mechanisms having, for example, separate shafts. Such separate drive mechanisms are not preferred since it would require additional components and space requirements.

Second tuft block 50 may be a fixed section either having fixed bristles or bristles which can move independently of each other by being mounted on an elastomeric base. Preferably, however, second tuft block 50 moves or oscillates. For example, second tuft block 50 may move in and out in a direction generally perpendicular to the outer surface of head 34. This would result in a vibrating section. Any suitable drive mechanism 44 may be used to accomplish this in and out vibrating motion such as the type of drive section described in U.S. Pat. No. Re. 35,941, the disclosure of which being incorporated herein by reference in its entirety except where inconsistent with the express teachings of the present invention. Alternatively, the vibrating section could be free floating without a positive drive. Other forms of movement of second tuft block 50 could be parallel to the longitudinal axis of head 34. However, second tuft block 50 may move perpendicular to the longitudinal axis of head 34.

For the above embodiments, a polymer battery 26 is embedded within the toothbrush handle. For the manual toothbrush 10, polymer battery 26 provides power to light source 24. For the powered toothbrush 30, polymer battery 26 provides power to drive mechanism 44 and may provide power to light source 24 if one is provided. Polymer battery 26 contains no heavy metals, making it environmentally safe. Polymer battery 26 also contains no alkaline, making it physically safe. Polymer battery 26 preferably is inexpensive and rechargeable, making it an economical power source for the toothbrush. Polymer battery 26 may be rechargeable mechanically, as shown in FIGS. 1 and 2, but may also be rechargeable chemically or photochemically. The small size of polymer battery 26 saves space in the toothbrush handle, enabling the handle to be smaller and saving on materials of construction. The flexible nature of polymer battery 26 enables it to be shaped to fit into the toothbrush housing design. The flexible design also enables polymer battery 26 to be formed about the periphery of the toothbrush handle so that the handle may be made thinner.

Polymer battery 26 may be constructed in accordance with any of the teachings of U.S. Pat. Nos. 4,801,512, 4,804,594, 5,527,640, 5,665,490, 5,733,683, and 5,888,672, the disclosures of which being incorporated by reference herein in their entireties except where inconsistent with the express teachings of the present invention. Preferably, however, the materials making up the positive and negative electrodes of polymer battery 26 include, but are not limited to, poly(3(2-fluorophenyl)thiophene), poly(3(3-fluorophenyl)thiophene), poly(3(2,4-fluorophenyl) thiophene), poly(3(3,4-fluorophenyl)thiophene), poly(3(3,4-difluorophenyl)thiophene), poly(3(3,5-difluoro-phenyl) thiophene), poly(3(3,4,5-trifluorophenyl)thiophene), lithium alloy/polypyrrole, tetramethyl/-ethyl/propyl/ butylammonium trifluoromethane sulphonate, tetraalkyl ammonium salts, alcoholic hydroxy groups, polyaniline, polyacetylene, polyparaphenylene, poly(p-phenylene sulfide), poly(p-phenylene vinylene), poly(2,5-thienylene vinylene), etc.

Polymer batteries having these configurations have been shown to exhibit high charging capacities with excellent cycling efficiencies. The voltage and ampage required for polymer battery 26 will depend on the toothbrush version (manual or powered) and the energy needed to power the light source and/or the drive mechanism.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A toothbrush assembly, comprising:
   a head connected to a neck, said head having a plurality of bristles extending outwardly therefrom;
   a handle connected to said neck, said handle having a light-transmissive portion;
   a light source provided in the said handle; and
   a polymer battery provided in said handle and electrically coupled to said light source to provide power thereto.

2. A toothbrush assembly as recited in claim 1, wherein said light source comprises a light-emitting diode (LED).

3. A toothbrush assembly as recited in claim 1, wherein said polymer battery is rechargeable.

4. A toothbrush assembly as recited in claim 2, wherein said polymer battery is rechargeable mechanically, chemically, or photochemically.

5. A toothbrush assembly as recited in claim 1, wherein said polymer battery comprises at least one electrode made of an electrically conductive polymer selected from the group consisting of poly(3(2-fluorophenyl)thiophene), poly (3(3-fluorophenyl)thiophene), poly(3(2,4-fluorophenyl)- thiophene), poly(3(3,4-fluorophenyl)thiophene), poly(3(3,4-difluorophenyl)thiophene), poly(3(3,5-difluoro-phenyl) thiophene), poly(3(3,4,5-trifluorophenyl)thiophene), lithium alloy/polypyrrole, tetramethyl/-ethyl/propyl/ butylammonium trifluoromethane sulphonate, tetraalkyl ammonium salts, alcoholic hydroxy groups, polyaniline, polyacetylene, polyparaphenylene, poly(p-phenylene sulfide), poly(p-phenylene vinylene), and poly(2,5-thienylene vinylene).

6. A toothbrush assembly as recited in claim 1, wherein said polymer battery is environmentally safe.

7. A toothbrush assembly as recited in claim 1, wherein said polymer battery is flexible.

8. A toothbrush assembly, comprising:
   a head connected to a neck, said head having a plurality of bristles extending outwardly therefrom;
   a handle connected to said neck, said handle having a light-transmissive portion;
   a drive mechanism provided in the said handle; and
   a polymer battery provided in said handle and electrically coupled to said drive mechanism to provide power thereto.

9. A toothbrush assembly as recited in claim 8, further comprising a light source provided in said handle and electrically coupled to said polymer battery to receive power therefrom.

10. A toothbrush assembly as recited in claim 9, wherein said light source comprises a light-emitting diode (LED).

11. A toothbrush assembly as recited in claim 8, wherein said polymer battery is rechargeable.

12. A toothbrush assembly as recited in claim 11, wherein said polymer battery is rechargeable mechanically, chemically, or photochemically.

13. A toothbrush assembly as recited in claim 8, wherein said polymer battery comprises at least one electrode made of an electrically conductive polymer selected from the group consisting of poly(3(2-fluorophenyl)thiophene), poly(3(3-fluorophenyl)thiophene), poly(3(2,4-fluorophenyl)thiophene), poly(3(3,4-fluorophenyl)thiophene), poly(3(3,4-difluorophenyl)thiophene), poly(3(3,5-difluoro-phenyl)thiophene), poly(3(3,4,5-trifluorophenyl)thiophene), lithium alloy/polypyrrole, tetramethyl/-ethyl/propyl/butylammonium trifluoromethane sulphonate, tetraalkyl ammonium salts, alcoholic hydroxy groups, polyaniline, polyacetylene, polyparaphenylene, poly(p-phenylene sulfide), poly(p-phenylene vinylene), and poly(2,5-thienylene vinylene).

14. A toothbrush assembly as recited in claim 8, wherein said polymer battery is environmentally safe.

15. A toothbrush assembly as recited in claim 8, wherein said polymer battery is flexible.

16. A toothbrush assembly as recited in claim 9, wherein said polymer battery is rechargeable.

17. A toothbrush assembly as recited in claim 16, wherein said polymer battery is rechargeable mechanically, chemically, or photochemically.

18. A toothbrush assembly as recited in claim 9, wherein said polymer battery comprises at least one electrode made of an electrically conductive polymer selected from the group consisting of poly(3(2-fluorophenyl)thiophene), poly(3(3-fluorophenyl)thiophene), poly(3(2,4-fluorophenyl)thiophene), poly(3(3,4-fluorophenyl)thiophene), poly(3(3,4-difluorophenyl)thiophene), poly(3 (3,5-di fluoro-phenyl)thiophene), poly(3(3,4,5-trifluorophenyl)thiophene), lithium alloy/polypyrrole, tetramethyl/-ethyl/propyl/butylammonium trifluoromethane sulphonate, tetraalkyl ammonium salts, alcoholic hydroxy groups, polyaniline, polyacetylene, polyparaphenylene, poly(p-phenylene sulfide), poly(p-phenylene vinylene), and poly(2,5-thienylene vinylene).

19. A toothbrush assembly as recited in claim 9, wherein said polymer battery is environmentally safe.

20. A toothbrush assembly as recited in claim 9, wherein said polymer battery is flexible.

* * * * *